United States Patent [19]

Albertson

[11] 4,009,171
[45] Feb. 22, 1977

[54] N-ACYLATED-11-OXYGENATED-2,6-METHANO-3-BENZAZOCINE INTERMEDIATES

[75] Inventor: Noel F. Albertson, Schodack, N.Y.

[73] Assignee: Sterling Drug Inc., New York, N.Y.

[22] Filed: Feb. 21, 1974

[21] Appl. No.: 444,487

[52] U.S. Cl. .................. 260/293.54; 260/DIG. 13; 424/267

[51] Int. Cl.$^2$ ..................... C07D 221/26

[58] Field of Search ............................. 260/293.54

[56] References Cited

UNITED STATES PATENTS

| | | | |
|---|---|---|---|
| 2,733,330 | 5/1973 | Schubert et al. | 260/293.54 |
| 3,639,407 | 2/1972 | Clarke et al. | 260/293.54 |
| 3,700,734 | 10/1972 | Robinson et al. | 260/293.54 |
| 3,891,657 | 6/1975 | Monkovic et al. | 260/293.54 |

OTHER PUBLICATIONS

Saito et al., J. Org. Chem. 26, 4536–4540 (1961).

*Primary Examiner*—G. Thomas Todd
*Attorney, Agent, or Firm*—Theodore C. Miller; B. Woodrow Wyatt

[57] ABSTRACT

11-Oxygenated-2,6-methano-3-benzazocines N-alkylated by alkylmethyl, haloalkenylmethyl, alkynylmethyl, cycloalkylmethyl, cycloalkenylmethyl, cycloalkyl or 2-cycloalkenyl are prepared directly by N-alkylation of the corresponding N-H intermediates or indirectly by N-acylation of the corresponding N-H intermediates followed by reduction of the resulting N-acylated intermediates and are useful as antagonists of narcotic analgesics.

3 Claims, No Drawings

N-ACYLATED-11-OXYGENATED-2,6-METHANO-3-BENZAZOCINE INTERMEDIATES

This invention relates to N-alkylated-11-oxygenated-2,6-methano-3-benzazocines useful as antagonists of narcotic analgesics and to intermediates and processes useful in the preparation thereof.

In its N-alkylated-11-oxygenated 2,6-methano-3-benzazocine aspect the invention sought to be patented is 1,2,3,4,5,6-hexahydro-3-Q-6-R-8-X-11-Y-11-Z-2,6-methano-3-benzazocine of the formula

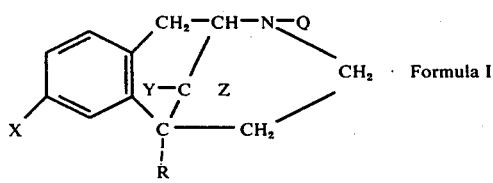

wherein:

Q is alkylmethyl having 3–6 carbon atoms, alkenylmethyl having 3–6 carbon atoms, haloalkenylmethyl having 3–6 carbon atoms and having 1–3 halogen atoms bonded to ethylenic carbon, alkynylmethyl having 3–6 carbon atoms, cycloalkylmethyl or cycloalkenylmethyl having 3–7 ring carbon atoms and having 4–10 total carbon atoms, or cycloalkyl or 2-cycloalkenyl having 5–7 ring carbon atoms and having 5–8 total carbon atoms;

R is methyl or ethyl;

X is hydrogen, hydroxy, acetoxy or methoxy;

Y and Z taken together are oxo; or

Y taken alone is hydrogen, methyl or ethyl when Z taken alone is hydroxy or acetoxy; and Z taken alone is hydrogen or methyl when Y taken alone is hydroxy or acetoxy;

or an acid-addition salt thereof.

In one of its intermediate aspects the invention sought to be patented is 1,2,3,4,5,6-hexahydro-3-Q'CO-6-R-8-X'-11-Y'-11-Z'-2,6-methano-3-benzazocine of the formula

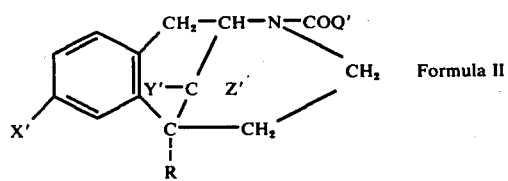

wherein:

Q' is alkyl having 2–5 carbon atoms, alkenyl having 2–5 carbon atoms, haloalkenyl having 2–5 carbon atoms and having 1–3 halogen atoms bonded to ethylenic carbon, alkynyl having 2–5 carbon atoms or cycloalkyl or cycloalkenyl having 3–7 ring carbon atoms and having 3–9 total carbon atoms;

R is methyl or ethyl;

X' is hydrogen, hydroxy, acetoxy, methoxy or Q'COO;

Y' is hydrogen, methyl or ethyl when Z' is hydroxy, acetoxy or Q'COO; and

Z' is hydrogen or methyl when Y' is hydroxy, acetoxy or Q'COO.

In its other intermediate aspect the invention sought to be patented is 1,2,3,4,5,6-hexahydro-6-R-8-X''-11-Y''-11-Z''-2,6-methano-3-benzazocine of the formula

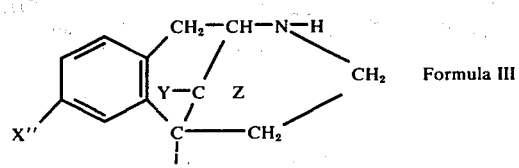

wherein

R is methyl or ethyl;

X'' is hydrogen, hydroxy or acetoxy;

Y and Z taken together are oxo; or

Y taken alone is hydrogen, methyl or ethyl when Z taken alone is hydroxy or acetoxy; and Z taken alone is hydrogen or methyl when Y taken alone is hydroxy or acetoxy;

or an acid-addition salt thereof.

The compounds of Formula II are useful as intermediates for preparing compounds of Formula I by the third process described below. The compounds of Formula III are useful as intermediates for preparing compounds of Formula I by the first process described below and for preparing compounds of Formula II by the second process described below.

In one of its process aspects the invention sought to be patented is the process which comprises N-alkylating 1,2,3,4,5,6-hexahydro-6-R-8-X-11-Y-11-Z-2,6-methano-3-benzazocine of the formula

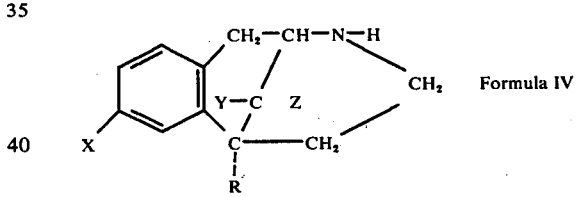

with Q-An in the presence of an acid-absorber to yield 1,2,3,4,5,6-hexahydro-3-Q-6-R-8-X-11-Y-11-Z-2,6-methano-3-benzazocine of Formula I wherein:

Q is alkylmethyl having 3–6 carbon atoms, alkenylmethyl having 3–6 carbon atoms, haloalkenylmethyl having 3–6 carbon atoms and having 1–3 halogen atoms bonded to ethylenic carbon, alkynylmethyl having 3–6 carbon atoms, cycloalkylmethyl or cycloalkenylmethyl having 3–7 ring carbon atoms and having 4–10 total carbon atoms, or cycloalkyl or 2-cycloalkenyl having 5–7 ring carbon atoms and having 5–8 total carbon atoms;

R is methyl or ethyl;

X is hydrogen, hydroxy, acetoxy or methoxy;

Y and Z taken together are oxo; or

Y taken alone is hydrogen, methyl or ethyl when Z taken alone is hydroxy or acetoxy;

Z taken alone is hydrogen or methyl when Y taken alone is hydroxy or acetoxy; and An is the anion of a strong organic or inorganic acid.

In a second process aspect the invention sought to be patented is the process which comprises N-acylating 1,2,3,4,5,6-hexahydro-6-R-8-X-11-Y''-11-Z''-2,6-methano-3-benzazocine of the formula

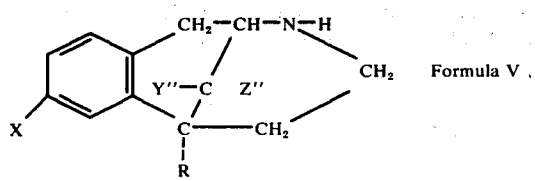

Formula V with an active acylating form of an acid of the formula Q'COOH to yield 1,2,3,4,5,6-hexahydro-3-Q'CO-6-R-8-X'-11-Y'-11-Z'-2,6-methano-3-benzazocine of Formula II wherein:

Q' is alkyl having 2–5 carbon atoms, alkenyl having 2–5 carbon atoms, haloalkenyl having 2–5 carbon atoms and having 1–3 halogen atoms bonded to ethylenic carbon, alkynyl having 2–5 carbon atoms or cycloalkyl or cycloalkenyl having 3–7 ring carbon atoms and having 3–9 total carbon atoms;

R is methyl or ethyl;

X is hydrogen, hydroxy, acetoxy or methoxy;

X' is hydrogen, hydroxy, acetoxy, methoxy or Q'COO;

Y' is hydrogen, methyl or ethyl when Z' is hydroxy, acetoxy or Q'COO;

Y'' is hydrogen, methyl or ethyl when Z'' is hydroxy or acetoxy;

Z' is hydrogen or methyl when Y' is hydroxy, acetoxy or Q'COO; and

Z'' is hydrogen or methyl when Y'' is hydroxy or acetoxy.

In a third process aspect the invention sought to be patented is the process which comprises reducing 1,2,3,4,5,6-hexahydro-3-Q'CO-6-R-8-X'-11-Y'-11-Z'-2,6-methano-3-benzazocine of Formula II with a reducing agent effective to reduce Q'CO to Q'CH$_2$ without affecting any ethylenic or acetylenic linkages to yield 1,2,3,4,5,6-hexahydro-3-Q'CH$_2$-6-R-8-X*-11-Y*-11-Z*-2,6-methano-3-benzazocine of the formula

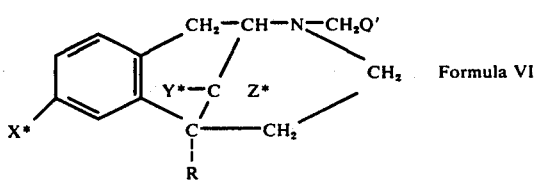

Formula VI wherein:

Q' is alkyl having 2–5 carbon atoms, alkenyl having 2–5 carbon atoms, haloalkenyl having 2–5 carbon atoms and having 1–3 halogen atoms bonded to ethylenic carbon, alkynyl having 2–5 carbon atoms or cycloalkyl or cycloalkenyl having 3–7 ring carbon atoms and having 3–9 total carbon atoms;

R is methyl or ethyl;

X' is hydrogen, hydroxy, acetoxy, methoxy or Q'COO;

X* is hydrogen, hydroxy or methoxy;

Y' is hydrogen, methyl or ethyl when Z' is hydroxy, acetoxy or Q'COO;

Y* is hydrogen, methyl or ethyl when Z* is hydroxy;

Z' is hydrogen or methyl when Y' is hydroxy, acetoxy or Q'COO; and

Z* is hydrogen or methyl when Y* is hydroxy.

When Q in Formula I and in Q-An is alkylmethyl, it is, for example, propyl, butyl, isobutyl or 3,3-dimethylbutyl.

When Q in Formula I and in Q-An is alkenylmethyl, it is, for example, allyl, 2-methyl-2-propenyl, 2-butenyl, 3-methyl-2-butenyl or 2,3-dimethyl-2-butenyl.

When Q in Formula I and Q-An is haloalkenylmethyl, halo is fluoro, chloro or bromo and haloalkenylmethyl is, for example, 2-fluoro-2-propenyl, 2-chloro-2-propenyl, 3-chloro-2-propenyl, 2-bromo-2-propenyl, 3-bromo-2-propenyl, 3,3-difluoro-2-propenyl, 2,3-difluoro-2-propenyl, 2,3-difluoro-3-chloro-2-propenyl, 3-chloro-2-butenyl, 2-chloro-3-methyl-2-butenyl, 4-chloro-2,3-dimethyl-3-butenyl, 2-bromo-2-butenyl or 2,3-dichloro-2-butenyl.

When Q in Formula I and in Q-An is alkynylmethyl, it is, for example, propargyl, 2-butynyl, 3-butynyl or 2,2-dimethyl-3-butynyl.

When Q in Formula I and in Q-An is cycloalkylmethyl, it is, for example, cyclopropylmethyl, cyclobutylmethyl, cyclopentylmethyl, cyclohexylmethyl, cycloheptylmethyl or 2,4,6-trimethylcyclohexylmethyl.

When Q in Formula I and in Q-An is cycloalkenylmethyl, it is, for example, 1-cyclopropenylmethyl, 1-cyclopentenylmethyl, 1-cyclohexenylmethyl, 2-cyclohexenylmethyl or 3-cyclohexenylmethyl.

When Q in Formula I and in Q-An is cycloalkyl, it is, for example, cyclopentyl, cyclohexyl, cycloheptyl or 4,4-dimethylcyclohexyl.

When Q in Formula I and in Q-An is 2-cycloalkenyl, it is, for example, 2-cyclopentenyl, 2-cyclohexenyl, 2-cycloheptenyl or 4,4-dimethyl-2-cyclohexenyl.

When Q' in Formulas II and VI and Q'COOH is alkyl, Q'CO is, for example, propionyl, butyryl, isobutyryl or 3,3-dimethylbutanoyl.

When Q' in Formulas II and VI and Q'COOH is alkenyl, Q'C is, for example, acryloyl, 2-methylacryloyl, 3-methylacryloyl, 3,3-dimethylacryloyl or 2,3,3-trimethylacryloyl.

When Q' in Formulas II and VI and in Q'COOH is haloalkenyl, Q'CO is, for example, 2-fluoroacryloyl, 2-chloroacryloyl, 3-chloroacryloyl, 2-bromoacryloyl, 3-bromoacryloyl, 3,3-difluoroacryloyl, 2,3-difluoroacryloyl, 2,3-difluoro-3-chloroacryloyl, 3-chloro-2-methylacryloyl, 2-chloro-3,3-dimethylacryloyl, 4-chloro-2,3-dimethylbutenoyl, 2-bromo-2-methylacryloyl or 2,3-dichloro-2-methylacryloyl.

When Q' in Formulas II and VI and in Q'COOH is alkynyl, Q'CO is, for example, propiolyl, 2-butynoyl, 3-butynoyl or 2,2-dimethyl-3-butynoyl.

When Q' in Formulas II and VI and in Q'COOH is cycloalkyl, Q'CO is, for example, cyclopropylcarbonyl, cyclobutylcarbonyl, cycloentylcarbonyl, cyclohexylcarbonyl, cycloheptylcarbonyl or 2,4,6-trimethylcyclohexylcarbonyl.

When Q' in Formulas II and VI and in Q'COOH is cycloalkenyl, Q'CO is, for example, 1-cyclopropenylcarbonyl, 1-cyclopentylcarbonyl, 1-cyclohexenylcarbonyl, 2-cyclohexenylcarbonyl or 3-cyclohexenylcarbonyl.

The compounds of Formulas I-VI are racemic. The features

and C..Z (for Z taken alone) in Formula I and the corresponding features in Formulas II-VI represent bonds oriented below the plane of the page if the plane of the tetralin moiety is considered to be in the plane of the page. When Y is hydrogen, methyl or ethyl, it is referred to as equatorial (eq) with respect to the tetralin moiety and trans with respect to R; the 11-carbon atom is RS in chirality; and the compound is in the β-series of benzomorphans as designated by May and coworkers (see Nathan B. Eddy and Everette L. May, Synthetic Analgesics, Pergamon Press, Part IIB, 1966, pp. 117–137). Z is then hydroxy or acetoxy and is referred to as axial. When Z is hydrogen or methyl, it is referred to as axial (ax) with respect to the tetralin moiety and cis with respect to R; the 11-carbon atom is SR in chirality; and the compound is in the α-series of compounds as designated by May and coworkers. Y is then hydroxy or acetoxy and is referred to as equatorial. The chiralities of the 2-carbon atom and 6-carbon atom are RS and SR, respectively.

The compounds of Formulas I and III are amino bases and react with organic and inorganic acids to form acid-addition salts. Due to the presence of the basic amino grouping, the free base forms represented by Formulas I, III, IV, and VI above react with organic and inorganic acids to form acid-addition salts. The acid-addition salt forms are prepared from any organic or inorganic acid. They are obtained in conventional fashion, for instance either by direct mixing of the base with the acid or, when this is not appropriate, by dissolving either or both of the base and the acid separately in water or an organic solvent and mixing the two solutions, or by dissolving both the base and the acid together in a solvent. The resulting acid-addition salt is isolated by filtration, if it is insoluble in the reaction medium, or by evaporation of the reaction medium to leave the acid-addition salt as a residue. The acid moieties or anions in these salt forms are in themselves neither novel nor critical and therefore can be an acid anion or acid-like substance capable of salt formation with the base.

Representative acids for the formation of the acid-addition salts include formic acid, acetic acid, isobutyric acid, alpha-mercaptopropionic acid, trifluoroacetic acid, malic acid, fumaric acid, succinic acid, succinamic acid, tannic acid, glutamic acid, tartaric acid, oxalic acid, pyromucic acid, citric acid, lactic acid, glycolic acid, gluconic acid, saccharic acid, ascorbic acid, penicillin, benzoic acid, phthalic acid, salicylic acid, 3,5-dinitrobenzoic acid, anthranilic acid, cholic acid, 2-pyridinecarboxylic acid, pamoic acid, 3-hydroxy-2-naphthoic acid, picric acid, quinic acid, tropic acid, 3-indoleacetic acid, barbituric acid, sulfamic acid, methanesulfonic acid, ethanesulfonic acid, isethionic acid, benzenesulfonic acid, p-toluenesulfonic acid, butylarsonic acid, methanephoshonic acid, acidic resin, hydrofluoric acid, hydrochloric acid, hydrobromic acid, hydriodic acid, perchloric acid, nitric acid, sulfuric acid, phoshoric acid, arsenic acid, and the like. All of the acid-addition salts are useful as sources of the free bases by reaction with a stronger base. Thus, if one or more characteristics such as solubility, molecular weight, physical appearance, toxicity or the like of a given base of acid-addition salt thereof render that form unsuitable for the purpose at hand, it can be readily converted to another, more suitable form. For pharmaceutical purposes, acid-addition salts of relatively non-toxic, pharmaceutically-acceptable acids, for example hydrochloric acid, lactic acid, tartaric acid, and the like, are of course employed. Either the free bases or the acid-addition salts thereof may crystallize as crystalline solvates with solvent of crystallization in integral of fractional amounts, for example, as the tetrahydrate or sesquihydrate.

The manner and process of making and using the invention and the best mode of carrying it out will now be described so as to enable any person skilled in the art to which it pertains to make and use it.

The first process aspect is a direct (one-step) synthesis and the second and third process aspects are an indirect (two-step) synthesis of preparing the compounds of Formula I.

In the direct synthesis the tertiary-amino compounds of Formula I are prepared by N-alkylating the corresponding secondary-amino compounds of Formula IV with an alkylating agent of the formula Q-An in the presence of an acid-absorber. Although An in the formula Q-An is the anion of any strong organic or inorganic acid which does not interfere with the alkylation and especially halide, for example, chloride or bromide, or arylsulfonate, for example, p-toluenesulfonate, Q-An wherein An is bromide is particularly preferred. Although any effective acid-absorber and especially alkali metal bicarbonates are contemplated, sodium bicarbonate is particularly preferred. Ordinarily it is preferable to use a diluent such as a lower alkanol, for example, methanol or ethanol, or an N,N-(di-loweralkyl)-lower alkanamide, for example, N,N-dimethylformamide or N,N-dimethylacetamide. The N-alkylation may be carried out with or without heating or cooling.

In the indirect synthesis the tertiary-amino compounds of Formula VI are prepared by first N-acylating the corresponding secondary-amino compounds of Formula V and then reducing the resulting N-acyl compounds of Formula II.

The N-acylation step is accomplished with an active acylating form of an acid of the formula Q'COOH such as an acid halide, for example, the acid chloride or the acid bromide, the acid anhydride or a mixed anhydride, for example, the mixed anhydride with trifluoroacetic acid; with or without a diluent; with or without an acid-absorber; and with or without heating or cooling. The diluent and the acid-absorber may be the same, for example, pyridine, or different, for example, chloroform and triethylamine, respectively. If the compound of Formula V has a free hydroxyl at the 8-position or the 11-position, such hydroxyl may also be acylated in the N-acylation step, depending on the quantity and/or reactivity of the active acylating form.

The reduction step is accomplished with a reducing agent effective to reduce $Q'CO$ to $Q'CH_2$ without affecting any ethylenic or acetylenic linkages, for example, lithium aluminum hydride, triisobutylaluminum or diisobutylaluminum hydride. A diluent is preferably used, for example, tetrahydrofuran. The reduction may be carried out with or without heating or cooling. Any acylated hydroxyl at the 8-position or 11-position is converted into hydroxyl under the conditions of the reduction.

The compounds of Formulas I, III, IV and V having 8-acetoxy and/or 11-acetoxy are prepared by selective acetylation of the corresponding hydroxy compounds with an active acetylating form of acetic acid. In preparing the compounds of Formulas III, IV and V having 8-acetoxy and/or 11-acetoxy the secondary-amino moiety of the corresponding hydroxy compounds must be protected from acetylation, for example, by N-benzylation. After acetylation the N-benzyl can be removed by catalytic hydrogenation.

The 8,11-diacetoxy compounds of Formulas I, III, IV and V are obtained by diacetylating the corresponding 8,11-dihydroxy compounds with two or more molar equivalents of the active acetylating form, for example, acetic anhyride.

The 8-acetoxy-11-hydroxy compounds of Formulas I, III, IV and V are obtained by selectively monoacetylating the corresponding 8,11-dihydroxy compounds, for example, by forming the phenolate salt (the 8-hydroxy is phenolic) with sodium methoxide, then acetylating with acetyl chloride.

The 8-hydroxy-11-acetoxy compounds of Formulas I, III, IV and V are obtained either by selectively monoacetylating the corresponding 8,11-dihydroxy compounds or by selectively monodeacetylating the corresponding 8,11-diacetoxy compounds. The selective monoacetylation is effected, for example, with one molar equivalent of acetic trifluoroacetic mixed anhydride, which is formed from acetyl chloride and trifluoroacetic acid. The selective monodeacetylation is effected, for example, with an amino base such as benzylamine.

The 8-methoxy compounds of Formulas I and II are prepared by the direct process starting from the corresponding 8-methoxy compounds or by the indirect process starting from the corresponding 8-methoxy compounds or by O-methylating the corresponding 8-hydroxy compounds of Formulas I or II with, for example, diazomethane.

The 8-hydroxy compounds of Formula III are prepared by O-demethylating the corresponding 8-methoxy compounds with, for example, concentrated hydrobromic acid. The 8-methoxy-11-acetoxy compounds are transformed by concentrated hydrobromic acid to the corresponding 8,11-dihydroxy compounds of Formula III, which must be selectively remonoacetylated as described above if the 8-hydroxy-11-acetoxy compounds of Formula III are desired.

The starting materials for the preparation of the compounds of Formulas I-VI are prepared according to the methods of May and coworkers (J. Org. Chem., 25, 1386 (1960) and 26, 188–193, 1621–1624, 1954–1957 and 4536–4540 (1961)).

The starting materials for the compounds of Formulas I-VI are the 1,2,3,4,5,6-hexahydro-3,3-dimethyl-6-R-8-X°-11-oxo-2,6-methano-3-benzazocine quaternary ammonium bromides (or other anion) of the formula

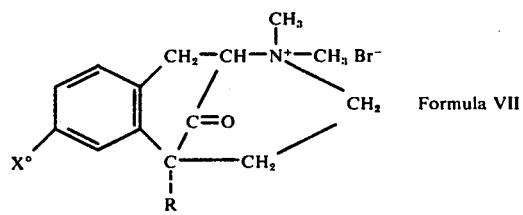

wherein R is methyl or ethyl and X° is hydrogen or methoxy.

The compounds of Formulas III, IV and V wherein Y or Y" is hydroxy and Z or Z" is hydrogen or methyl are prepared by first catalytically hydrogenating with platinum oxide or methylating with methylmagnesium iodide or methyllithium the corresponding compounds of Formula VII to form the 1,2,3,4,5,6-hexahydro-3,3-dimethyl-6-R-8-X°-11-hydroxy-11-Z°-2,6-methano-3-benzazocine quaternary ammonium bromides (or other anion) of the formula

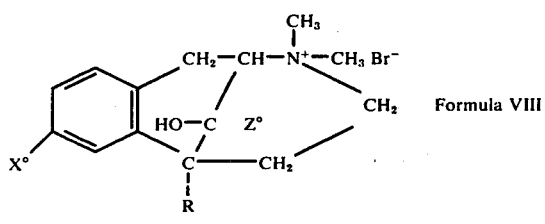

wherein R is methyl or ethyl, X° is hydrogen or methoxy and Z° is hydrogen or methyl.

On the other hand the compounds of Formulas III, IV and V wherein Y or Y" is hydrogen, methyl or ethyl and Z or Z" is hydroxy are prepared by first N-monodemethylating thermally in refluxing 1-octanol or 1-nonanol the corresponding compounds of Formula VII and then catalytically hydrogenating with platinum oxide, methylating with methylmagnesium iodide or methyllithium or ethylating with ethylmagnesium bromide the resulting 1,2,3,4,5,6-hexahydro-3-Q°-6-R-8-X°-11-oxo-2,6-methano-3-benzazocines of the formula

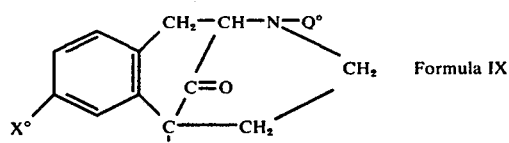

wherein Q° is methyl, R is methyl or ethyl and X° is hydrogen or methoxy to form the 1,2,3,4,5,6-hexahydro-3-Q°-6-R-8-X°-11-hydroxy-11-Y°-2,6-methano-3-benzazocines of the formula

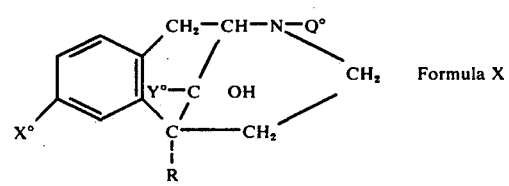

wherein Q° is methyl, R is methyl or ethyl, X° is hydrogen or methoxy and Y° is hydrogen, methyl or ethyl.

Formation of axial Z° and equatorial 11-hydroxy in the compounds of Formula VIII is attributed by May and coworkers to the influence of quaternary ammonium moiety on the hydrogenation or methylation of the compounds of Formula VII. Contrastingly, formation of equatorial Y° and axial 11-hydroxy in the compounds of Formula X wherein Q° is methyl is attributed to the influence of the tertiary amine moiety on the hydrogenation, methylation or ethylation of the compounds of Formula IX wherein Q° is methyl.

Thermal N-monodemethylation in 1-nonanol of the compounds of Formula VIII affords the corresponding 1,2,3,4,5,6-hexahydro-3-Q°-6-R-8-X°-11-hydroxy-11-Z°-2,6-methano-3-benzazocines of the formula

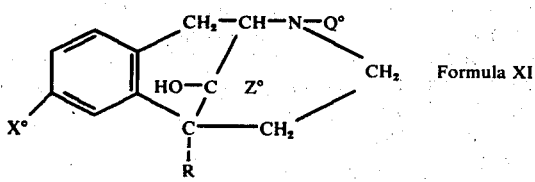

Formula XI wherein Q° is methyl, R is methyl or ethyl, X° is hydrogen or methoxy and Z° is hydrogen or methyl.

N-Demethylation of the compounds of Formulas IX, X and XI wherein Q° is methyl is accomplished in two stages. Replacement of N-methyl by N-cyano is effected with cyanogen bromide, affording the corresponding compounds of Formulas IX, X and XI wherein Q° is cyano. N-cyano is then removed by hydrolysis with dilute hydrochloric acid and the corresponding compounds of Formulas IX, X and XI wherein Q° is hydrogen are formed.

The following examples illustrate the invention. Structures of compounds are inferred from reaction types. Confirmations of structures are made by analyses of the elements, ultraviolet spectra, infrared spectra, nuclear magnetic resonance spectra and/or mass spectra. Courses of reactions and homogeneities of products are ascertained by thin layer chromatography and/or gas-liquid chromatography. Melting points are uncorrected unless otherwise indicated.

EXAMPLE 1

A. A solution of 1,2,3,4,5,6-hexahydro-3-methyl-6-methyl-8-methoxy-11-oxo-2,6-methano-3-benzazocine (IX: Q° = R = CH$_3$, X° = CH$_3$O; the compound described as 2′-methoxy-2,5-dimethyl-9-oxo-6,7-benzomorphan at J. Org. Chem., 25, 1388 (1960); 3.53 g.) in chloroform (30 ml.) was added dropwise to a solution of cyanogen bromide (2.5 g.) in chloroform (25 ml.). The mixture was stirred under reflux (for 18 hr.), then extracted with dilute hydrochloric acid (5%). Desiccation and concentration of the chloroform layer afforded a red-yellow solid, recrystallization of which from ether afforded 1,2,3,4,5,6-hexahydro-3-cyano-6-methyl-8-methoxy-11-oxo-2,6-methano-3-benzazocine (IX: Q° = CN, R = CH$_3$, X° = CH$_3$O; 1.8 g.).

A mixture of 1,2,3,4,5,6-hexahydro-3-cyano-6-methyl-8-methoxy-11-oxo-2,6-methano-3-benzazocine (1.8 g.) and dilute hydrochloric acid (5%) was stirred in a nitrogen atmosphere under reflux (for 16 hr.), basified, saturated with salt and extracted with ether. Desiccation and concentration of the ether extracts afforded 1,2,3,4,5,6-hexahydro-6-methyl-8-methoxy-11-oxo-2,6-methano-3-benzazocine (IX: Q° = H, R = CH$_3$, X° = CH$_3$O; 1.5 g.), a pale-yellow oil.

A mixture of 1,2,3,4,5,6-hexahydro-6-methyl-8-methoxy-11-oxo-2,6-methano-3-benzazocine (2.18 g.) and hydrobromic acid (48%, 20 ml.) was stirred under reflux (for 30 min.), basified with dilute ammonia and extracted with chloroform. Desiccation and concentration of the chloroform extracts afforded a tan solid (1.1 g.), recrystallization of which from acetone afforded 1,2,3,4,5,6-hexahydro-b-methyl-8-hydroxy-11-oxo-2,6-methano-3-benzazocine (III: R = CH$_3$, X″ = HO, Y + Z = O; 0.4 g.), a white solid.

B. N-Demethylation of 1,2,3,4,5,6-hexahydro-3-methyl-6-ethyl-8-methoxy-11-oxo-2,6-methano-3-benzazocine (IX: Q° = CH$_3$, R = CH$_3$CH$_2$, X° = CH$_3$O; the compound described as 5-ethyl-2′-methoxy-2-methyl-9-oxo-6,7-benzomorphan at J. Org. Chem., 26, 4539 (1961) by the cyanogen bromide-hydrochloric acid sequence gives 1,2,3,4,5,6-hexahydro-6-ethyl-8-methoxy-11-oxo-2,6-methano-3-benzazocine (IX: Q° = H, R = CH$_3$CH$_2$, X° = CH$_3$O), O-demethylation of which with hydrobromic acid gives 1,2,3,4,5,6-hexahydro-6-ethyl-8-hydroxy-11-oxo-2,6-methano-3-benzazocine (III: R = CH$_3$CH$_2$, X″ = HO, Y + Z = O).

C. N-Demethylation of 1,2,3,4,5,6-hexahydro-3-methyl-6-methyl-11-oxo-2,6-methano-3-benzazocine (IX: Q° = R = CH$_3$, X° = H; the compound described as 2,5-dimethyl-9-oxo-6,7-benzomorphan at J. Org. Chem., 26, 1623 (1961)) by the cyanogen bromide-hydrochloric acid sequence gives 1,2,3,4,5,6-hexahydro-6-methyl-11-oxo-2,6-methano-3-benzazocine (III: R = CH$_3$, X″ = H, Y + Z = O).

D. N-Benzylation of 1,2,3,4,5,6-hexahydro-6-methyl-8-hydroxy-11-oxo-2,6-methano-3-benzazocine (part A) with benzyl chloride gives 1,2,3,4,5,6-hexahydro-3-benzyl-6-methyl-8-hydroxy-11-oxo-2,6-methano-3-benzazocine, acetylation of which with sodium methoxide and acetyl chloride gives 1,2,3,4,5,6-hexahydro-3-benzyl-6-methyl-8-acetoxy-11-oxo-2,6-methano-3-benzazocine, N-debenzylation of which by catalytic hydrogenation with palladium gives 1,2,3,4,5,6-hexahydro-6-methyl-8-acetoxy-11-oxo-2,6-methano-3-benzazocine (III; R = CH$_3$, X″ = CH$_3$COO, Y + Z = O).

E. A mixture of 1,2,3,4,5,6-hexahydro-6-methyl-8-hydroxy-11-oxo-2,6-methano-3-benzazocine (part A, 0.220 g.), cyclopropylmethyl bromide (0.200 g.), sodium bicarbonate (0.084 g.) and N,N-dimethylformamide (5 ml.) was stirred in a nitrogen atmosphere under reflux (for 2 hr.), then stripped of N,N-dimethylformamide. A solution of the residue in dilute hydrochloric acid (5%) was extracted with ether, neutralized and extracted with ether again. Desiccation and concentration of the latter ether extracts afforded 1,2,3,4,5,6-hexahydro-3-cyclopropylmethyl-6-methyl-8-hydroxy-11-oxo-2,6-methano-3-benzazocine (I: Q = CH$_2$CHCH$_2$CH$_2$, R = CH$_3$, X = HO, Y + Z = O) as a yellow oil, from which with methanesulfonic acid was obtained the methanesulfonate salt as another oil, from which with 1,5-naphthalenedisulfonic acid was obtained the crystalline 1,5-naphthalenedisulfonate tetrahydrate salt (220 mg., m.p. 287°–288° C.).

F. N-Alkylation of 1,2,3,4,5,6-hexahydro-6-ethyl-8-hydroxy-11-oxo-2,6-methano-3-benzazocine (part B) with cyclopropylmethyl bromide gives 1,2,3,4,5,6-hexahydro-3-cyclopropylmethyl-6-ethyl-8-hydroxy-11-oxo-2,6-methano-3-benzazocine (I: Q = CH$_2$CHCH$_2$CH$_2$, R = CH$_3$CH$_2$, X = HO, Y + Z = O).

G. N-Alkylation of 1,2,3,4,5,6-hexahydro-6-methyl-11-oxo-2,6-methano-3-benzazocine (part C) with cyclopropylmethyl bromide gives 1,2,3,4,5,6-hexahydro-3-cyclopropylmethyl-6-methyl-11-oxo-2,6-methano-3-benzazocine (I: Q = CH$_2$CHCH$_2$CH$_2$, R = CH$_3$, X = H, Y + Z = O).

H. N-Alkylation of 1,2,3,4,5,6-hexahydro-6-methyl-8-acetoxy-11-oxo-2,6-methano-3-benzazocine (part D) with cyclopropylmethyl bromide gives 1,2,3,4,5,6-hexahydro-3-cyclopropylmethyl-6-methyl-8-acetoxy-11-oxo-2,6-methano-3-benzazocine (I: Q = CH$_2$CHCH$_2$CH$_2$, R = CH$_3$, X = CH$_3$COO, Y + Z = O).

EXAMPLE 2

A. A solution of 1,2,3,4,5,6-hexahydro-3-methyl-6-methyl-8-methoxy-11(ax)-hydroxy-2,6-methano-3- benzazocine (X: Q° = R = CH₃, X° = CH₃O, Y° = H; the compound described as β-9-hydroxy-2'-methoxy-2,5-dimethyl-6,7-benzomorphan at J. Org. Chem., 26, 1956 (1961); 12.2 g.) in chloroform (85 ml.) was added slowly (during 2 hr.) with stirring to a solution of cyanogen bromide (5.5 g.) in chloroform (50 ml.), then concentrated. Ethyl acetate, water and charcoal were added to the residue. Filtration of the mixture and concentration of the filtrate afforded 1,2,3,4,5,6-hexahydro-3-cyano-6-methyl-8-methoxy-11(ax)-hydroxy-2,6-methano-3-benzazocine (X: Q° = CN, R = CH₃, X° = CH₃O, Y° = H; 9.7 g.), a yellow oil.

A mixture of 1,2,3,4,5,6-hexahydro-3-cyano-6-methyl-8-methoxy-11(ax)-hydroxy-2,6-methano-3-benzazocine (9.7 g.), water (164 ml.) and concentrated hydrochloric acid (33 ml.) was heated under reflux (for 8 hr.). Charcoal was added, the mixture was filtered and the filtrate was concentrated. Water and aqueous sodium hydroxide were added to the resulting pale-yellow crystals and the resulting oil was extracted with benzene-butanol. Desiccation and concentration of the benzene-butanol extracts afforded a pink syrup, which crystallized in ether. The crystals were refluxed with acetone, affording 1,2,3,4,5,6-hexahydro-6-methyl-8-methoxy-11(ax)-hydroxy-2,6-methano-3-benzazocine (IX: Q° = Y° = H, R = CH₃, X° = CH₃O; 7.03 g., m.p. 137°–139.7° C.).

A mixture of 1,2,3,4,5,6-hexahydro-6-methyl-8-methoxy-11(ax)-hydroxy-2,6-methano-3-benzazocine (7.03 g.) and hydrobromic acid (48%, 70 ml.) was heated under reflux (for 17 min.), then concentrated. Water and charcoal were added to the residue, the mixture was filtered and the filtrate was concentrated. The crystalline residue was stirred with acetone, affording 1,2,3,4,5,6-hexahydro-6-methyl-8-hydroxy-11(ax)-hydroxy-2,6-methano-3-benzazocine (III: R = CH₃, X'' = HO, Z = OH, Y = H) hydrobromide (6.66 g., m.p. 239°–242° C., m.p. 240°–242° C. after recrystallization from methanol-ether). The free base from another preparation had m.p. 257°–260° C.

B. A mixture of 1,2,3,4,5,6-hexahydro-6-methyl-8-hydroxy-11(ax)-hydroxy-2,6-methano-3-benzazocine hydrobromide (part A, 2.70 g.), allyl bromide (1.21 g.), sodium bicarbonate (2.70 g.) and N,N-dimethylformamide (40 ml.) was stirred under reflux (for 2 hr.), then filtered. The filter cake was washed with ethanol and the filtrate was concentrated. Water and ether were added to the residue. The ether layer was separated, washed with water and stripped of ether. The crystalline residue was recrystallized from ether, affording 1,2,3,4,5,6-hexahydro-3-allyl-6-methyl-8-hydroxy-11(ax)-hydroxy-2,6-methano-3-benzazocine (I: Q = CH₂CH=CH₂, R = CH₃, X = HO, Y = H, Z = OH; 1.55 g., corrected m.p. 176.8°–180.2° C.).

C. N-Alkylation of 1,2,3,4,5,6-hexahydro-6-methyl-8-methoxy-11(ax)-hydroxy-2,6-methano-3-benzazocine (part A) with allyl bromide gives 1,2,3,4,5,6-hexahydro-3-allyl-6-methyl-8-methoxy-11(ax)-hydroxy-2,6-methano-3-benzazocine (I: Q = CH₂CH=CH₂, R = CH₃, X = CH₃O, Y = H, Z = OH).

D. Diacetylation of 1,2,3,4,5,6-hexahydro-3-allyl-6-methyl-8-hydroxy-11(ax)-hydroxy-2,6-methano-3-benzazocine (part D) with acetic anhydride gives 1,2,3,4,5,6-hexahydro-3-allyl-6-methyl-8-acetoxy-11(ax)-acetoxy-2,6-methano-3-benzazocine (I: Q = CH₂CH=CH₂, R = CH₃, X = CH₃COO, Y = H, Z = OCOCH₃).

E. Monoacetylation of 1,2,3,4,5,6-hexahydro-3-allyl-6-methyl-8-hydroxy-11(ax)-hydroxy-2,6-methano-3-benzazocine (part D) with sodium methoxide and acetyl chloride gives 1,2,3,4,5,6-hexahydro-3-allyl-6-methyl-8-acetoxy-11(ax)-hydroxy-2,6-methano-3-benzazocine (I: Q = CH₂CH=CH₂, R = CH₃, X = CH₃COO, Y = H, Z = OH).

F. Monoacetylation of 1,2,3,4,5,6-hexahydro-3-allyl-6-methyl-8-hydroxy-11ax)-hydroxy-2,6-methano-3-benzazocine (part D) with acetic trifluoroacetic mixed anhydride or, alternatively, monodeacetylation of 1,2,3,4,5,6-hexahydro-3-allyl-6-methyl-8-acetoxy-11(ax)-acetoxy-2,6-methano-3-benzazocine (part H) with benzylamine gives 1,2,3,4,5,6-hexahydro-3-allyl-6-methyl-8-hydroxy-11(ax)-acetoxy-2,6-methano-3-benzazocine (I: Q = CH₂CH=CH₂, R = CH₃, % = HO, Y = H, Z = OCOCH₃).

EXAMPLE 3

A. A mixture of 1,2,3,4,5,6-hexahydro-6-methyl-8-hydroxy-11(ax)-hydroxy-2,6-methano-3-benzazocine (part A of example 2, 0.6586 g.), dimethylallyl bromide (0.393 g.), sodium bicarbonate (0.455 g.) and N,N-dimethylformamide (11 ml.) was refluxed (for 2.5 hr.), then filtered. The filtrate was concentrated. The residue was extracted with isopropyl acetate. Concentration of the isopropyl acetate extract afforded a crude product (0.67 g., m.p. 153°–158.5° C.). After several unsuccessful attempts to purify the crude product by recrystallization, a solution of part (0.35 g.) of it in dilute hydrochloric acid was extracted with ether, then basified with ammonia, then extracted with isopropyl acetate. Desiccation and concentration of the isopropyl acetate extracts afforded 1,2,3,4,5,6-hexahydro-3-(3-methyl-2-butenyl)-6-methyl-8-hydroxy-11(ax)-hydroxy-2,6-methano-3-benzazocine (I: Q = CH₂CH=C(CH₃)₂, R = CH₃, X = HO, Y = H, Z = OH; 0.300 g., corrected m.p. 180.0°–181.2° C.).

B. N-Alkylation of 1,2,3,4,5,6-hexahydro-6-methyl-8-hydroxy-11(ax)-hydroxy-2,6-methano-3-benzazocine (part A of example 2) with cis-1,3-dichloro-1-propene gives 1,2,3,4,5,6-hexahydro-3-(3-chloro-2-propenyl)-6-methyl-8-hydroxy-11(ax)-hydroxy-2,6-methano-3-benzazocine (I: Q = cis-CH₂CH=CHCl, R = CH₃, X = HO, Y = H, Z = OH).

C. N-Alkylation of 1,2,3,4,5,6-hexahydro-6-methyl-8-hydroxy-11(ax)-hydroxy-2,6-methano-3-benzazocine (part A of example 2) with bromocyclopentane gives 1,2,3,4,5,6-hexahydro-3-cyclopentyl-6-methyl-8-hydroxy-11(ax)-hydroxy-2,6-methano-3-benzazocine (I: Q = $\overline{CH(CH_2)_3CH_2}$, R = CH₃, X = HO, Y = H, Z = OH).

D. N-Alkylation of 1,2,3,4,5,6-hexahydro-6-methyl-8-hydroxy-11(ax)-hydroxy-2,6-methano-3-benzazocine (part A of example 2) with 3-bromocyclohexene gives 1,2,3,4,5,6-hexahydro-3-(2-cyclohexenyl)-6-methyl-8-hydroxy-11(aX)-hydroxy-2,6-methano-3-benzazocine (I: Q = $\overline{CHCH=CHCH_2CH_2CH_2}$, R = CH₃, X = HO, Y = H, Z = OH).

EXAMPLE 4

A. Cyclopropanecarbonyl chloride (2.0 g.) was added dropwise with stirring to a mixture of 1,2,3,4,5,6-hexahydro-6-methyl-8-hydroxy-11(ax)-hydroxy-2,6-methano-3-benzazocine hydrobromide (part A of example 2, 3.00 g.), ethanol (20 ml.), potassium carbonate (4.0 g.) and water (10.0 ml.) and stirring was continued at room temperature (for 3 hr.).

The mixture was filtered, the filter cake was washed with ethanol and the filtrate was concentrated. Water and benzene-butanol were added to the residue. The benzene-butanol layer was washed with dilute hydrochloric acid, then water, dried, filtered and concentrated, affording 1,2,3,4,5,6-hexahydro-3-cyclopropanecarbonyl-6-methyl-8-hydroxy-11(ax)-hydroxy-2,6-methano-3-benzazocine (II: Q' = CHCH$_2$CH$_2$, R = CH$_3$, X' = HO, Y' = H, Z' = OH) plus possibly also 1,2,3,4,5,6-hexahydroxy-3-cyclopropanecarbonyl-6-methyl-8-cyclopropanecarboxy-11(ax)-hydroxy-2,6-methano-3-benzazocine (II: Q' = CHCH$_2$CH$_2$, R = CH$_3$, X' = CH$_2$CH$_2$CHCOO, Y' = H, Z' = OH), 1,2,3,4,5,6-hexahydro-3-cyclopropanecarbonyl-6-methyl-8-hydroxy-11(ax)-cyclopropanecarboxy-2,6-methano-3-benzazocine (II: Q' = CHCH$_2$CH$_2$, R = CH$_3$, X' = HO, Y' = H, Z' = OCOCHCH$_2$CH$_2$) and/or 1,2,3,4,5,6-hexahydro-3-cyclopropanecarbonyl-6-methyl-8-cyclopropanecarboxy-11(ax)-cyclopropanecarboxy-2,6-methano-3-benzazocine (II: Q' = CHCH$_2$CH$_2$, R = CH$_3$, X' = CH$_2$CH$_2$CHCOO, Y' = H, Z' = OCOCHCH$_2$CH$_2$) as a yellow syrup (3.2 g.).

B. A mixture of the yellow syrup from part A (3.2 g.), lithium aluminum hydride (1.6 g.) and tetrahydrofuran was stirred under reflux for (6.5 hr.). Water (1.6 ml.) in tetrahydrofuran was added, and the resulting solids were extracted with tetrahydrofuran and methanol. Ethereal hydrogen chloride was added to methanol solutions of the products of the extractions and the resulting crystalline solids were combined and recrystallized from methanol, affording 1,2,3,4,5,6-hexahydro-3-cyclopropylmethyl-6-methyl-8-hydroxy-11(ax)-hydroxy-2,6-methano-3-benzazocine (I: Q = CH$_2$CHCH$_2$CH$_2$, R = CH$_3$, X = HO, Y = H, Z = OH) hydrochloride (1.55 g., corrected m.p. 289.0°–290.4° C.).

Triisobutylaluminum or diisobutylaluminum hydride can be used instead of lithium aluminum hydride in this reduction.

C. N-Acylation of 1,2,3,4,5,6-hexahydro-6-hexahydro-6-methyl-8-hydroxy-11(ax)-hydroxy-2,6-methano-3-benzazocine (part A of example 2) with propionic anhydride gives 1,2,3,4,5,6-hexahydro-3-propionyl-6-methyl-8-hydroxy-11(ax)-hydroxy-2,6-methano-3-benzazocine (II: Q' = CH$_2$CH$_3$, R = CH$_3$, X' = HO, Y' = H, Z' = OH).

D. N-Acylation of 1,2,3,4,5,6-hexahydro-6-methyl-8-hydroxy-11(ax)-hydroxy-2,6-methano-3-benzazocine (part A of example 2) with 3,3-dimethylacryloyl chloride gives 1,2,3,4,5,6-hexahydro-3-(3,3-dimethylacryloyl)-6-methyl-8-hydroxy-11(ax)-hydroxy-2,6-methano-3-benzazocine (II: Q' = CH=C(CH$_3$)$_2$, R = CH$_3$, X' = HO, Y' = H, Z' = OH).

E. N-Acylation of 1,2,3,4,5,6-hexahydro-6-methyl-8-hydroxy-11(ax)-hydroxy-2,6-methano-3-benzazocine (part A of example 2) with propiolyl chloride gives 1,2,3,4,5,6-hexahydro-3-propiolyl-6-methyl-8-hydroxy-11(ax)-hydroxy-2,6-methano-3-benzazocine (II: Q' = C≡CH, R = CH$_3$, X' = HO, Y' = H, Z' = OH).

F. N-Acylation of 1,2,3,4,5,6-hexahydro-6-methyl-8-hydroxy-11(ax)-hydroxy-2,6-methano-3-benzazocine (part A of example 2) with 1-cyclopentenylcarbonyl chloride gives 1,2,3,4,5,6-hexahydro-3-(1-cyclopentenylcarbonyl)-6-methyl-8-hydroxy-11(ax)-hydroxy-2,6-methano-3-benzazocine (II: Q' = C=CHCH$_2$CH$_2$CH$_2$, R = CH$_3$, X' = HO, Y' = H, Z' = OH).

G. Reduction of 1,2,3,4,5,6-hexahydro-3-propionyl-6-methyl-8-hydroxy-11(ax)-hydroxy-2,6-methano-3-benzazocine (part C) with lithium aluminum hydride gives 1,2,3,4,5,6-hexahydro-3-propyl-6-methyl-8-hydroxy-11(ax)-hydroxy-2,6-methano-3-benzazocine (I: Q = CH$_2$CH$_2$CH$_3$, R = CH$_3$, X = HO, Y = H, Z = OH).

H. Reduction of 1,2,3,4,5,6-hexahydro-3-(3,3-dimethylacryloyl)-6-methyl-8-hydroxy-11(ax)-hydroxy-2,6-methano-3-benzazocine with lithium aluminum hydride gives 1,2,3,4,5,6-hexahydro-3-(3-methyl-2-butenyl)-6-methyl-8-hydroxy-11(ax)-hydroxy-2,6-methano-3-benzazocine, the compound of example 3.

I. Reduction of 1,2,3,4,5,6-hexahydro-3-propiolyl-6-methyl-8-hydroxy-11(ax)-hydroxy-2,6-methano-3-benzazocine with lithium aluminum hydride gives 1,2,3,4,5,6-hexahydro-3-propargyl-6-methyl-8-hydroxy-11(ax)-hydroxy-2,6-methano-3-benzazocine (I: Q = CH$_2$C≡CH, R = CH$_3$, X = HO, Y = H, Z = OH).

J. Reduction of 1,2,3,4,5,6-hexahydro-3-(1-cyclopentenylcarbonyl)-6-methyl-8-hydroxy-11(ax)-hydroxy-2,6-methano-3-benzazocine (part F) with lithium aluminum hydride gives 1,2,3,4,5,6-hexahydro-3(1-cyclopentylmethyl)-6-methyl-8-hydroxy-11(ax)-hydroxy-2,6-methano-3-benzazocine (I: Q = CH$_2$C=CHCH$_2$CH$_2$CH$_2$, R = CH$_3$, X = HO, Y = H, Z = OH).

EXAMPLE 5

A. A solution of 1,2,3,4,5,6-hexahydro-3-methyl-6-methyl-8-methoxy-11-methyl-11(ax)-hydroxy-2,6-methano-3-benzazocine (X: Q° = R = Y° = CH$_3$, X° = CH$_3$O; the compound described as β-9-hydroxy-2'-methoxy-2,5,9-trimethyl-6,7-benzomorphan at J. Org. Chem., 26, 192 (1961); 8.55 g.) in chloroform (57 ml.) was added slowly to a solution of cyanogen bromide (3.7 g.) in chloroform (33 ml.). The mixture was filtered. More cyanogen bromide (0.5 g.) was added to the filtrate and the solution was refluxed (for 1 hr. 45 min., later for 8½ hr.), then concentrated. An ether solution of the residue was washed with water, dried, treated with charcoal and concentrated. Recrystallization of the resulting crystals (3.0 g.) from ethanol afforded 1,2,3,4,5,6-hexahydro-3-cyano-6-methyl-8-methoxy-11-methyl-11(ax)-hydroxy-2,6-methano-3-benzazocine (X: Q° = CN, R = Y° = CH$_3$, X° = CH$_3$O; 2.69 g., m.p. 125°–126.5° C.).

A mixture of 1,2,3,4,5,6-hexahydro-3-cyano-6-methyl-8-methoxy-11-methyl-11(ax)-hydroxy-2,6methano-3-benzazocine (2.7 g.), concentrated hydrochloric acid (10 ml.) and water (50 ml.) was refluxed (for 8 hr.), treated with charcoal and filtered. Basification with aqueous sodium hydroxide of a solution of the residue in water and recrystallization of the resulting solid (1.7 g.) from acetone afforded 1,2,3,4,5,6-hexahydro-6-methyl-8-methoxy-11-methyl-11(ax)-hydroxy-2,6-methano-3-benzazocine (X: Q° = H, R = Y° = CH$_3$, X° = CH$_3$O; m.p. 147°–150° C.).

A mixture of 1,2,3,4,5,6-hexahydro-6-methyl-8-methoxy-11-methyl-11(ax)-hydroxy-2,6-methano-3-benzazocine (1.60 g.) and hydrobromic acid (48%, 16 ml.) was refluxed (for 22 min.), then concentrated. Acetone and later N,N-dimethylformamide and charcoal were added and the mixture was filtered. The filtrate was stripped of solvents, affording 1,2,3,4,5,6-hexahydro-6-methyl-8-hydroxy-11-methyl-11(ax)-hydroxy-2,6-methano-3-benzazocine (III: R = Y =

$CH_3$, X″ = HO, Z = OH) hydrobromide (2.40 g.) as a syrup,

B. N-Demethylation of 1,2,3,4,5,6-hexahydro-3-methyl-6-methyl-8-methoxy-11-ethyl-11(ax)-hydroxy-2,6-methano-3-benzazocine (X: Q° = R = $CH_3$, X° = $CH_3O$, Y° = $CH_3CH_2$; the compound described as β-9-ethyl-9-hydroxy-2′-methoxy-2,5-dimethyl-6,7-benzomorphan at J. Org. Chem., 26, 4540 (1961)) by the cyanogen bromide-hydrochloric acid sequence gives 1,2,3,4,5,6-hexahydro-3-cyano-6-methyl-8-methoxy-11-ethyl-11(ax)-hydroxy-2,6-methano-3-benzazocine (X: Q° = CN, R = $CH_3$, X° = $CH_3O$, Y° = $CH_3CH_2$), O-demethylation of which with hydrobromic acid gives 1,2,3,4,5,6-hexahydro-6-methyl-8-hydroxy-11-ethyl-11(ax)-hydroxy-2,6-methano-3-benzazocine (III: R = $CH_3$, X″ = HO, Y = $CH_3CH_2$, Z = OH).

C. A mixture of 1,2,3,4,5,6-hexahydro-6-methyl-8-hydroxy-11-methyl-11(ax)-hydroxy-2,6-methano-3-benzazocine hydrobromide (part A, 2.0 g.), dimethylallyl bromide (0.89 g.), sodium bicarbonate (2 g.) and N,N-dimethylformamide (25 ml.) was stirred under reflux (for 1.5 hr.) then concentrated. The residue was triturated with ether and filtered. The filtrate was treated with charcoal and extracted with dilute hydrochloric acid. The acid extract was basified with ammonia and extracted with ether. Hydrogen chloride was added to the ether extract and the mixture was concentrated. The product (0.9 g.) crystallized in ether-ethanol and was recrystallized from isopropyl alcohol-acetone, affording 1,2,3,4,5.6-hexahydro-3-(3-methyl-2-butenyl)-6-methyl-8-hydroxy-11-methyl-11(ax)-hydroxy-2,6-methano-3-benzazocine (I: Q = $CH_2CH=C(CH_3)_2$, R = Y = $CH_3$, X = HO, Z = OH) hydrochloride (m.p. 215°–218° (C.).

D. N-Alkylation of 1,2,3,4,5,6-hexahydro-6-methyl-8-hydroxy-11-ethyl-11(ax)-hydroxy-2,6-methano-3-benzazocine (part B) with dimethylallyl bromide gives 1,2,3,4,5,6-hexahydro-3-(3-methyl-2-butenyl)-6-methyl-8-hydroxy-11-ethyl-11(ax)-hydroxy-2,6-methano-3-benzazocine (I: Q = $CH_2CH=C(CH_3)_2$, R = $CH_3$, X = HO, Y = $CH_3CH_2$, Z = OH).

EXAMPLE 6

A. A solution of 1,2,3,4,5,6-hexahydro-3-methyl-6-methyl-8-methoxy-11(eq)-hydroxy-11-methyl-2,6-methano-3-benzazocine (XI: Q° = R = Z° = $CH_3$, X° = $CH_3$; prepared from the picrate salt of the compound described as α-9-hydroxy-2′-methoxy-2,5,9-trimethyl-6,7-benzomorphan at J. Org. Chem., 26, 191 (1961); 14.5 g.) in chloroform (90 ml.) was added slowly with stirring to a solution of cyanogen bromide (6.05 g.) in chloroform (60 ml.). The mixture was refluxed (for 3 hr.), then concentrated. The residue was partitioned between dilute hydrochloric acid and benzene. The dilute hydrochloric acid layer was extracted with ether. Evaporation of the ether afforded a red syrup (7.0 g.). The benzene layer was concentrated. The resulting yellow syrup formed crystals, recrystallization of which from ethyl acetate-hexane afforded 1,2,3,4,5.6-hexahydro-3-cyano-6-methyl-8-hydroxy-11(eq)-hydroxy-11-methyl-2,6-methano-3-benzazocine (XI: Q° = CN, R = Z° = $CH_3$, X° = $CH_3O$; 5.43 g., m.p. 121°–126° C.). Treatment of the red syrup with more cyanogen bromide afforded an additional quantity of product (0.3 g., m.p. 121°–125° C.).

A mixture of 1,2,3,4,5,6-hexahydro-3-cyano-6-methyl-8-methoxy-11(eq)-hydroxy-11-methyl-2,6-methano-3-benzazocine (5.73 g.), concentrated hydrochloric acid (18 ml.) and water (90 ml.) was stirred at reflux (for 8 hr.), then concentrated. The residue was recrystallized from water, affording 1,2,3,4,5,6-hexahydro-6-methyl-8-methoxy-11(eq)-hydroxy-11-methyl-2,6-methano-3-benzazocine (XI: Q° = H, R = Z° = $CH_3$, X° = $CH_3O$) hydrochloride (4.0 g., m.p. 150°–153° C.). Basification of the recrystallization liquor with aqueous sodium hydroxide and extraction of the resulting mixture with ether afforded a solid, recrystallization of which from ethanol-water afforded more product as the free base (0.5 g.).

A mixture of 1,2,3,4,5.6-hexahydro-6-methyl-8-methoxy-11(eq)-hydroxy-11-methyl-2,6-methano-3-benzazocine (0.50 g.) and hydrobromic acid (48%, 5.0 ml.) was refluxed (for 25 min.), then concentrated. Water was added to the residue and the mixture was reconcentrated. Water and aqueous ammonia were added to the residue and the resulting brown glop crystallized. Two recrystallizations of the crystals from methanol afforded 1,2,3,4,5.6-hexahydro-6-methyl-8-hydroxy-11(eq)-hydroxy-11-methyl-2,6-methano-3-benzazocine (III: R = Z = $CH_3$, X″ = Y = HO; 0.18 g., m.p. 268.5°–269° C.). Similar O-demethylation of 1,2,3,4,5.6-hexahydro-6-methyl-8-methoxy-11(eq)-hydroxy-11-methyl-2,6-methano-3-benzazocine hydrochloride (4.0 g.) afforded more product in two crops (1.25 g., 0.51 g.).

B. N-Demethylation of 1,2,3,4,5.6-hexahydro-3-methyl-6-methyl-8-methoxy-11(eq)-hydroxy-11-ethyl-2,6-methano-3-benzazocine (XI: Q° = R = $CH_3$, X° = $CH_3O$, Z° = $CH_2CH_3$; the compound described as α-9-hydroxy-2′-methoxy-2,5-dimethyl-6,7-benzomorphan at J. Org. Chem., 26, 1956 (1961)) by the cyanogen bromide-hydrochloric acid sequence gives 1,2,3,4,5,6-hexahydro-6-methyl-8-methoxy-11(eq)-hydroxy-11-ethyl-2,6-methano-3benzazocine (XI: Q° = H, R = $CH_3$, X° = HO, Z° = $CH_2CH_3$), O-demethylation of which with hydrobromic acid gives 1,2,3,4,5,6-hexahydro-6-methyl-8-hydroxy-11(eq)-hydroxy-11-ethyl-2,6-methano-3-benzazocine (III: R = $CH_3$, X″ = Y = HO, Z = $CH_2CH_3$).

C. Cyclopropanecarbonyl chloride (1.40 g.) was added dropwise to a solution of 1,2,3,4,5,6-hexahydro-6-methyl-8-hydroxy-11(eq)-hydroxy-11-methyl-2,6-methano-3-benzazocine (part A, 1.94 g.) in pyridine (35 ml.). The mixture was concentrated and the residue was partitioned between water and toluene-butanol. The toluene-butanol layer was concentrated and the residue was partitioned between dilute hydrochloric acid and ethyl acetate. The ethyl acetate layer was concentrated, affording 1,2,3,4,5,6-hexahydro-3-cyclopropanecarbonyl-6-methyl-8-hydroxy-11(eq)-hydroxy-11methyl-2,6-methano-3-benzazocine (II: Q′ = $\overline{CHCH_2CH_2}$, R = Z′ = $CH_3$, X′ = Y′ = HO) plus possibly also 1,2,3,4,5,6-hexahydro-3-cyclopropanecarbonyl-6-methyl-8-cyclopropanecarboxy-11(eq)-hydroxy-11-methyl-2,6-methano-3-benzazocine (II: Q′ = $\overline{CHCH_2CH_2}$, R = Z′ = $CH_3$, X′ = $\overline{CH_2CH_2CHCOO}$, Y′ = HO), 1,2,3,4,5,6-hexahydro-3-cyclopropanecarbonyl-6-methyl-8-hydroxy-11(eq)-cyclopropanecarboxy-11-methyl-2,6-methano-3-benzazocine (II: Q′ = $\overline{CHCH_2CH_2}$, R = Z′ = $CH_3$, X′ = HO, Y′ = $\overline{CH_2CH_2CHCOO}$) and/or 1,2,3,4,5,6-hexahydro-3-cyclopropanecarbonyl-6-methyl-8-cyclopropanecarboxy-11(eq)-cyclopropanecarboxy-11-methyl-2,6-methano-3-benzazocine (II: Q′ = $\overline{CHCH_2CH_2}$, R = Z′ = $CH_3$, X′ = Y′ = $\overline{CH_2CH_2CHCOO}$) as a syrup (2.8 g.).

D. N-Acylation of 1,2,3,4,5,6-hexahydro-6-methyl-8-hydroxy-11(eq)-hydroxy-11-ethyl-2,6-methano-3-benzazocine (part B) with cyclopropanecarbonyl chloride gives 1,2,3,4,5.6-hexahydro-3-cyclopropanecarbonyl-6-methyl-8-hydroxy-11-(eq)-hydroxy-11-ethyl-2,6-methano-3-benzazocine (II: Q' = $\overline{CHCH_2CH_2}$, R = CH$_3$, X' = Y' = HO, Z' = CH$_2$CH$_3$).

E. A solution of the syrup from part C (2.8 g.) in tetrahydrofuran was added to a mixture of lithium aluminum hydride (1.0 g.) in tetrahydrofuran and the mixture was refluxed (for 4 hr.). More tetrahydrofuran was added to dissolve the white crystals which separated when the mixture was allowed to stand. A solution of water (2.0 ml.) in tetrahydrofuran was then added dropwise and the mixture was filtered. The filtrate was concentrated, affording a foam (2.0 g.). The foam was taken up in methanol and mixture was filtered. Ethereal hydrogen chloride was added to the filtrate, affording crystals (1.84 g., m.p. 140°–144° C.). The crystals failed to recrystallize from acetonitrile, but recrystallized from methanol-ether, affording 1,2,3,4,5,6-hexahydro-3-cyclopropylmethyl-6-methyl-8-hydroxy-11(eq)-hydroxy-11-methyl-2,6-methano-3-benzazocine (I: Q = CH$_2$$\overline{CHCH_2CH_2}$, R = Z = CH$_3$, X = Y = HO) hydrochloride sesquihydrate (m.p. 157.5°–163° C.).

F. Reduction of 1,2,3,4,5,6-hexahydro-3-cyclopropanecarbonyl-6-methyl-8-hydroxy-11(eq)-hydroxy-11-ethyl-2,6-methano-3-benzazocine (part D) with lithium aluminum hydride gives 1,2,3,4,5,6-hexahydro-3-cyclopropylmethyl-6-methyl-8 hydroxy-11(eq)-hydroxy-11-ethyl-2,6-methano-3benzazocine (I: Q = CH$_2$$\overline{CHCH_2CH_2}$, R = CH$_3$, X = Y = HO, Z = CH$_2$CH$_3$).

The useful properties of the compounds of this invention were demonstrated by standard pharmacological procedures readily carried out by technicians having ordinary skill in pharmacological test procedures, so that the actual determination of the numerical biological data definitive for a particular test compound can be ascertained without the need for any extensive experimentation. Thus, in the test procedure used the compounds of Examples 1E, 2B, 3A, 4B, 5C and 6E were found to be useful as analgesic antagonists.

The test procedure used has been described in detail by Harris and Pierson (J. Pharmacol. Exp. Ther., 143, 141 (1964)) at pages 141–143 as "a. Rat tail-flick procedure" and "c. Antagonism of strong analgesics."

The following results were obtained when the componds of Exampes 1E and 6E were tested against phenazocine hydrobromide and the compounds of Examples 2B, 3A, 4B and 5C wrere tested against meperidine hydrochloride. The AD$_{50}$ value in each case is expressed in terms of the free base.

| Compound of | AD$_{50}$ Value (mg./kg.) |
|---|---|
| Example 1E | 0.16 |
| Example 2B | 0.115 |
| Example 3A | 6.8 |
| Example 4B | 0.056 |
| Example 5C | 0.62 |
| Example 6E | 0.0026 |

After this application was filed it was discovered that the C-11 configuration of the compounds of parts A, B and C of Example 5 is opposite to the configuration described herein, that is, the 11-hydroxy is not axial but equatorial, as shown by Noel F. Albertson, J. Med. Chem., 18, 619–621 (1975).

I claim:

1. 1,2,3,4,5,6-Hexahydro-3-Q'CO-6-R-8-X'-11-Y'-11-Z'-2,6-methano-3-benzazocine of the formula

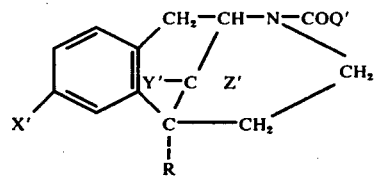

wherein
Q' is cyclopropyl;
R is methyl;
X' is hydroxy or Q'COO; and
Y' is hydrogen when Z' is hydroxy or Q'COO; or
Y' is hydroxy or Q'COO when Z' is methyl.

2. 1,2,3,4,5,6-Hexahydro-3-cyclopropanecarbonyl-6-methyl-8-hydroxy-11(ax)-hydroxy-2,6-methano-3-benzazocine according to claim 1.

3. 1,2,3,4,5,6-Hexahydro-3-cyclopropanecarbonyl-6-methyl-8-hydroxy-11(eq)-hydroxy-11-methyl-2,6-methano-3-benzazocine according to claim 1.

* * * * *

UNITED STATES PATENT AND TRADEMARK OFFICE
CERTIFICATE OF CORRECTION

PATENT NO. : 4,009,171
DATED : February 22, 1977
INVENTOR(S) : Noel F. Albertson It is certified that error appears in the above-identified patent and that said Letters Patent are hereby corrected as shown below:

Column 18, claim 1, the formula should read:

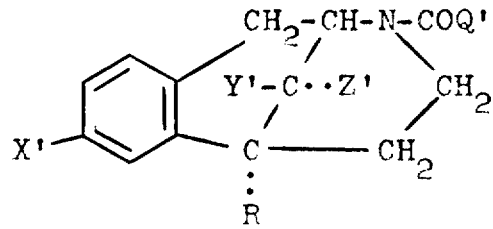

The corresponding correction (insertion of the two dots) should also be made in the specification in Formulas I, II, III, IV, V, VI, VIII, X and XI.

Signed and Sealed this

Third Day of July 1979

[SEAL]

Attest:

Attesting Officer

LUTRELLE F. PARKER
Acting Commissioner of Patents and Trademarks